United States Patent
Takada et al.

(10) Patent No.: US 12,186,733 B2
(45) Date of Patent: Jan. 7, 2025

(54) WATER-ABSORBING COMPOSITION AND PRODUCTION METHOD THEREFOR

(71) Applicant: KAO CORPORATION, Tokyo (JP)

(72) Inventors: Yuki Takada, Utsunomiya (JP); Takuya Kouta, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 655 days.

(21) Appl. No.: 17/433,685

(22) PCT Filed: Feb. 13, 2020

(86) PCT No.: PCT/JP2020/005564
§ 371 (c)(1),
(2) Date: Aug. 25, 2021

(87) PCT Pub. No.: WO2020/175153
PCT Pub. Date: Sep. 3, 2020

(65) Prior Publication Data
US 2022/0161231 A1   May 26, 2022

(30) Foreign Application Priority Data

Feb. 28, 2019 (JP) .................... 2019-036714

(51) Int. Cl.
*B01J 20/24* (2006.01)
*A61L 15/28* (2006.01)
*B01J 20/28* (2006.01)
*B01J 20/30* (2006.01)

(52) U.S. Cl.
CPC ............... *B01J 20/24* (2013.01); *A61L 15/28* (2013.01); *B01J 20/28007* (2013.01); *B01J 20/28026* (2013.01); *B01J 20/30* (2013.01); *A61L 2400/12* (2013.01); *B01J 2220/44* (2013.01)

(58) Field of Classification Search
None
See application file for complete search history.

(56) References Cited

U.S. PATENT DOCUMENTS

| | | |
|---|---|---|
| 2001/0011516 A1 | 8/2001 | Cantiani et al. |
| 2016/0333116 A1 | 11/2016 | Nakatani et al. |
| 2017/0283596 A1 | 10/2017 | Saito et al. |

FOREIGN PATENT DOCUMENTS

| | | | | |
|---|---|---|---|---|
| JP | 2005263858 A | | 9/2005 | |
| JP | 2008248053 A | * | 10/2008 | |
| JP | 2011140534 A | | 7/2011 | |
| JP | 2014170693 A | * | 9/2014 | |
| JP | 2015178099 A | | 10/2015 | |
| JP | 2016011392 A | | 1/2016 | |
| JP | 2016166258 A | | 9/2016 | |
| JP | 2016171074 A | * | 9/2016 | ............. H01G 11/06 |
| JP | 2016186018 A | | 10/2016 | |
| JP | 2017066283 A | | 4/2017 | |
| JP | 2017186528 A | | 10/2017 | |
| JP | 2018131573 A | | 8/2018 | |
| WO | WO-9802486 A1 | | 1/1998 | |
| WO | WO-2015012273 A1 | | 1/2015 | |
| WO | WO-2015064465 A1 | | 5/2015 | |
| WO | WO-2015107995 A1 | | 7/2015 | |

OTHER PUBLICATIONS

Sunrose Mac Series Technical Information, date unknown.*
International Search Report issued May 12, 2020 in PCT/JP2020/005564 (with English translation), 7 pages.
Cheng Shun Yang, "Textile Chemicals", Petrochemical Press, Aug. 2001, p. 390.
Extended European Search Report issued Nov. 2, 2022 in Patent Application No. 20763645.7, 7 pages.

* cited by examiner

Primary Examiner — Tanisha Diggs
(74) Attorney, Agent, or Firm — Element IP, PLC

(57) ABSTRACT

An absorbent composition containing cellulose nanofibers and a cellulose derivative and a method for making the same are disclosed. The cellulose derivative has a viscosity of 1000 mPa·s or higher in a 1 mass % aqueous solution at 25° C. and a degree of etherification of less than 0.9. The cellulose derivative is preferably at least one member selected from the group consisting of carboxymethyl cellulose, carboxyethyl cellulose, a carboxymethyl cellulose salt, and a carboxyethyl cellulose salt, more preferably a carboxymethyl cellulose salt, even more preferably sodium carboxymethyl cellulose.

16 Claims, No Drawings

WATER-ABSORBING COMPOSITION AND PRODUCTION METHOD THEREFOR

CROSS-REFERENCE TO RELATED APPLICATIONS

This application is the U.S. National Stage of International Application No. PCT/JP2020/005564, filed Feb. 13, 2020. This application claims priority to Japanese Patent Application No. 2019-036714, filed Feb. 28, 2019.

TECHNICAL FIELD

The present invention relates to an absorbent composition and a method for producing the same.

BACKGROUND ART

Cellulose nanofibers are fine fibers produced from pulp and so on and known as a material involving low environmental burdens in the production and disposal phases. Having high hydrophilicity and good thickening properties, cellulose fibers are expected for use in a broad range of fields such as foods, medical products, and coatings. However, dry cellulose nanofibers have low dispersibility in water because of high liability to aggregation. As an approach to solve this problem, patent literature 1 below discloses a dry solid comprising anionically modified cellulose nanofibers and a water-soluble polymer added in a specific ratio.

CITATION LIST

Patent Literature

Patent literature 1: US 2016/333116

SUMMARY OF INVENTION

The present invention provides an absorbent composition containing cellulose nanofibers and a cellulose derivative.

The cellulose derivative preferably has a viscosity of 1000 mPa·s or higher as measured in a 1 mass % aqueous solution at 25° C.

The cellulose derivative preferably has a degree of etherification of less than 0.9.

The present invention also provides a method for producing the absorbent composition. The absorbent composition is preferably produced by mixing the cellulose nanofibers and the cellulose derivative in a liquid and drying the resulting mixed solution.

DESCRIPTION OF EMBODIMENTS

Patent literature 1 proposes using cellulose nanofibers as a gelling agent or an absorbent material. However, the dry solid according to patent literature 1 has insufficient absorption performance for use as an absorptive material of absorbent articles.

The present invention provides an absorbent composition having improved absorption performance and a method for making the same.

The present invention will be described on the basis of its preferred embodiments. The absorbent composition of the present invention (hereinafter also referred to simply as the absorbent composition) contains cellulose nanofibers (hereinafter abbreviated as CNFs) and a cellulose derivative. A CNF is a fine fiber with a diameter of 3 to 500 nm and a length of 500 to 1000 nm.

CNFs can be produced by known processes, including nanofibrillation treatments of cellulose fibers and biosynthesis using bacteria such as acetic bacteria. The nanofibrillation treatments include physical processes, including a treatment in a defibrator, such as a high-pressure homogenizer; chemical processes, including an enzymatic treatment with, e.g., cellulase and catalytic oxidation; and combinations of the physical and chemical processes.

Examples of the cellulose fibers to be nanofibrillated include wood pulp, such as softwood pulp and hardwood pulp; cotton pulp, such as cotton linter and cotton lint; and non-wood pulp, such as straw pulp and bagasse pulp. They may be used either individually or as a combination of two or more thereof.

CNFs may have modified the hydroxyl groups on the cellulose molecular chains. Such modified CNFs include those having functional groups introduced to the cellulose hydroxy groups, such as those having their hydroxy group oxidized to carboxy group, esterified, or etherified. From the standpoint of improvement on dispersibility, it is preferable to use CNFs modified with an anionic group, namely anionically modified CNFs. Examples of the anionic group of the anionically modified CNFs include aldehyde, carboxy, sulfate, and phosphate. Carboxy and phosphate groups are preferred for achieving higher nanofibrillation.

Anionically modified CNFs can be obtained by known processes, such as oxidation of the hydroxy group of cellulose to an anionic group or reaction of the hydroxy group of cellulose with at least one of an anionic group-containing compound or its acid anhydride and derivatives thereof. For example, the hydroxy group of cellulose may be oxidized with an oxidizer, such as sodium hypochlorite and a bromide, such as sodium bromide, in the presence of 2,2,6,6-tetramethyl-1-piperidine-N-oxyl (TEMPO) as a catalyst (see, e.g., JP 2011-140632A).

The cellulose derivative is partially modified cellulose, including carboxymethyl cellulose, carboxyethyl cellulose, methyl cellulose, hydroxypropyl cellulose, hydroxypropylmethyl cellulose, hydroxyethyl cellulose, and their salts. The salt is preferably a water-soluble one, including at least one metal salt selected from an alkali metal salt, such as a sodium or potassium salt, and an alkaline earth metal salt, such as a calcium or magnesium salt. The absorbent composition may contain one of, or a combination of two or more of, these cellulose derivatives. From the viewpoint of effective prevention of CNFs aggregation, the cellulose derivative is preferably at least one compound selected from the group consisting of carboxymethyl cellulose, carboxyethyl cellulose, carboxymethyl cellulose salts, and carboxyethyl cellulose salts.

The cellulose derivative for use in the present invention has a viscosity of 1000 mPa·s or higher in a 1 mass % aqueous solution at 25° C. With a view to improving absorption capacity, the viscosity is preferably 4000 mPa·s or higher, more preferably 6,000 mPa·s or higher, preferably 30,000 mPa·s or lower, more preferably 20,000 mPa·s or lower, and specifically preferably 4,000 to 30,000 mPa·s, more preferably 6,000 to 20,000 mPa·s. The viscosity of the cellulose derivative in a 1 mass % aqueous solution at 25° C. can be measured with a Brookfield viscometer (TBV-10, from Toki Sangyo Co., Ltd.) equipped with a rotor No. 4 at 30 rpm for 60 seconds.

The cellulose derivative has a degree of etherification of lower than 0.9. With the view of increasing the absorption capacity, the degree of etherification is preferably 0.4 or higher, more preferably 0.5 or higher, preferably 0.8 or lower, more preferably 0.75 or lower, and specifically preferably 0.4 to 0.8, more preferably 0.5 to 0.75. The degree of etherification can be determined by the following method.

Determination of Degree of Etherification:

The degree of etherification can be determined by the ashing method. A precisely weighed quantity (ca. 0.7 g) of a sample (cellulose derivative) is wrapped in filter paper, put in a magnetic crucible, and thoroughly ashed at 600° C. After cooling, the ash is transferred to a 500 mL beaker, about 250 mL of water and 35 mL of 0.05 mol/L sulfuric acid are added thereto in that order, and the mixture is boiled for 30 minutes. After cooling, a phenolphthalein indicator is added, and the excess acid is determined by back titration with 0.1 mol/L potassium hydroxide. The degree of etherification is calculated by equation:

$$\text{Degree of etherification} = 162 \times A/(10000 - 80 \times A)$$

where A is the amount (mL) of 0.05 mol/L sulfuric acid consumed by bound alkali in 1 g of the sample.

The CNFs and the cellulose derivative are separable from the absorbent composition by filtration. The filtration can be carried out as follows. The absorbent composition containing CNFs and the cellulose derivative is diluted to a 0.1 mass % concentration with ion-exchanged water. The diluted aqueous solution is filtered by centrifugation at 12,000×g for 10 minutes through a 0.5 μm polytetrafluoroethylene filter. CNFs build up on the filter, while the cellulose derivative passes through the filter. CNFs and the cellulose derivative can thus be separated from each other.

The characteristics of the CNFs and cellulose derivative used in the absorbent composition, such as viscosity and degree of etherification, can be determined using the CNFs and the cellulose derivative separated from the absorbent composition.

It is known to use a dried mixed liquid of CNFs and a cellulose derivative with the view of improving water dispersibility of dry CNFs as taught in patent literature 1. The inventors of the present invention have investigated the relation between the dispersibility of CNFs and the cellulose derivative and, as a result, considered that the cellulose derivative having the above specified viscosity and degree of etherification effectively increases the water dispersibility of CNFs and thus completed the present invention. Containing the cellulose derivative having the above specified viscosity and degree of etherification, the absorbent composition of the present invention is capable of gelling and retaining a good amount of absorbed water, namely exhibits excellent absorption performance. The absorbent composition of the present invention is preferably used as an absorbent material of absorbent articles, such as diapers.

With a view to further improving absorption performance, the ratio of the CNF content designated C1 to the cellulose derivative content designated C2 in the absorbent composition, i.e., C1:C2, is preferably 1:1 to 1:100, more preferably 1:2 to 1:50, even more preferably 1:3 to 1:20. Throughout the description, all the contents are based on mass unless otherwise noted.

With a view to further improving water dispersibility of CNFs, the cellulose derivative preferably has a mass average molecular weight Mw of 5,000 to 1,000,000, more preferably 10,000 to 800,000, even more preferably 100,000 to 600,000. The mass average molecular weight can be determined by common gel permeation chromatography using, for example, HLC-8020 from Tosoh Corp. The columns used in the determination are chosen as appropriate to the predicted mass average molecular weight and ionic properties.

In order to increase the absorption rate thereby to improve absorption performance, CNFs preferably have the following characteristics. The average length of CNFs is preferably 500 nm or larger, more preferably 1,000 nm or larger, preferably 5,000 nm or smaller, more preferably 3,000 nm or smaller, and specifically preferably 500 to 5,000 nm, more preferably 1,000 to 3,000 nm. The average diameter of CNFs is preferably 3 nm or larger, more preferably 5 nm or larger, preferably 300 nm or smaller, more preferably 100 nm or smaller, and specifically preferably 3 to 300 nm, more preferably 5 to 100 nm.

The average length and diameter of CNFs may be measured as follows. Water or ethanol is added to the absorbent composition with a solids concentration, e.g., of 0.0001 mass % to prepare a dispersion. The dispersion is dispensed by drops onto mica and dried to make a sample to be observed. At least five CNFs are chosen at random under an atomic force microscope (Nanoscope III Tapping mode AFM, from Digital Instrument) and their lengths and thicknesses are measured using Point Probe NCH, from Nanosensors.

With the view of improving the absorption performance, the CNFs preferably have an average aspect ratio (length to diameter ratio) of 50 to 2,500, more preferably 75 to 2,000, even more preferably 100 to 1,500.

The CNFs and cellulose derivatives for use in the present invention may be purchased from the market. Examples of commercially available CNF products include Rheocrysta from DKS Co., Ltd., BiNFi-S from Sugino Machine Ltd., and Celish from Daicel FineChem Ltd. CNFs are generally sold in the form of an aqueous dispersion. Examples of commercially available cellulose derivative products include Cellogen from DKS Co., Ltd., CEKOL from Sansho Co., Ltd., and CMC Daicel from Daicel FineChem.

The absorbent composition may contain optional components other than the CNFs and cellulose derivative. Examples of useful optional components include fillers, pigments, dyes, preservatives, antioxidants, fragrances, deodorants, and antimicrobials. The content of any optional component, if added, in the absorbent composition is preferably not more than 10 mass %, more preferably 5 mass % or less. When two or more optional components are added, their total content is preferably within the above range.

The absorbent composition is a solid formed by drying. It is used as a dry solid in, for example, granular, particulate, fibrous, porous, or sheet form. The absorbent composition may be formed into any shape and size according to the intended use by an appropriate processing method, such as granulation. For use as, for example, an absorbent material of absorbent articles, the absorbent composition preferably has the form of dry particles preferably with a particle diameter of about 300 μm.

From the viewpoint of handling as an absorbent material, the water content of the absorbent composition is preferably not more than 15 mass %, more preferably 10 mass % or less.

When the absorbent composition is in sheet form, the thickness of the sheet is preferably 0.1 to 100 μm, more preferably 1 to 50 μm, even more preferably 3 to 10 μm.

The absorbent composition is preferably capable of absorbing at least 50 times, more preferably 100 or more times, even more preferably 200 or more times, its own weight in water. Although there is no upper limit for water absorption capacity, the upper limit would generally be 500 times its weight. The amount of water that can be absorbed and retained by the absorbent composition is obtained as a maximum liquid retention capacity determined in the method for evaluating gelation in Examples hereinafter given.

As stated earlier, the absorbent composition of the present invention is preferably used as an absorbent material of absorbent articles, such as diapers. Absorbent articles are used chiefly for the absorption and containment of bodily fluids, such as urine and menstrual blood, including disposable diapers, sanitary napkins, incontinence pads, and panty liners. Applicable absorbent articles are not limited to those listed above and broadly include any articles used to absorb discharged bodily fluids. An absorbent article is typically composed of a topsheet, a backsheet, and a liquid retentive absorbent member interposed between the topsheet and backsheet. The absorbent member is a main member for liquid absorption and comprises an absorbent material. The absorbent article may further include other various members depending on the intended use as is known to those skilled in the art.

The method for producing the absorbent composition of the present invention will then be described on the basis of its preferred embodiments. The method of the present invention includes mixing CNFs and the cellulose derivative in a liquid comprising a dispersing medium, such as water, (mixing step) and drying the resulting mixed solution (drying step).

In the method of the present invention, the above-described CNFs and cellulose derivative are used. The CNFs are used in the form dispersed in a medium, such as water, namely in the form of dispersion.

In the mixing step, a CNF dispersion and the cellulose derivative are mixed to prepare a mixed solution. In the mixed solution preparation, water or an alcoholic medium may be added. Examples of the alcoholic medium include monohydric alcohols, such as ethanol, 2-propyl alcohol, methanol, and butanol; ketones, such as acetone, methyl ethyl ketone, methyl isobutyl ketone, and cyclohexanone; and esters, such as ethyl acetate and butyl acetate.

To facilitate the mixing, the CNF content in the mixed solution is preferably 0.1 mass % or higher, more preferably 0.2 mass % or higher, preferably 1 mass % or lower, more preferably 0.8 mass % or lower, and specifically preferably 0.1 to 1 mass %, more preferably 0.2 to 0.8 mass %.

For the same purpose, the cellulose derivative content in the mixed solution is preferably 0.1 mass % or higher, more preferably 0.2 mass % or higher, preferably 1 mass % or lower, more preferably 0.8 mass % or lower, and specifically preferably 0.1 to 1 mass %, more preferably 0.2 to 0.8 mass %.

The CNF to cellulose derivative ratio in the mixed solution is preferably adjusted so that the CNF content to cellulose derivative content ratio in the absorbent composition, i.e., C1:C2, may fall in the above recited range.

With a view to uniformly disperse the CNFs and cellulose derivative in the mixed solution, the dispersing medium is preferably mainly composed of water. Specifically, the medium preferably has a water content of 80 mass % or higher, more preferably 90 mass % or higher, preferably lower than 100 mass %, and specifically preferably 80 to less than 100 mass %, more preferably 90 to less than 100 mass %.

In the mixing step the CNFs and cellulose derivative are dissolved in a dispersing medium to prepare a mixed solution. The process of dissolving, i.e., dispersing the CNFs and cellulose derivative in a medium is not particularly restricted, and any known dispersing process may be adopted, including shear mixing, ultrasonication, high-pressure jet treatment, shaking, and a combination thereof. Shear mixing may be achieved using shear apparatuses, such as a stirring machine. Ultrasonication may be carried out using ultrasonic processors, such as an ultrasonic homogenizer. High-pressure jet treatment may be performed using high-pressure jet dispersing machines, such as a pressure homogenizer. Shaking may be conducted using a paint shaker and the like. The mixing step may be carried out at room temperature (25° C.), or the mixing tank may be heated up to about 40° C.

The order of dispersing the CNFs and the cellulose derivative in the medium is not critical. The CNFs may be dispersed first, and the cellulose derivative may be dispersed in the resulting dispersion, or vise versa. The CNFs and the cellulose derivative may be added simultaneously into a mixing tank having a dispersing medium.

The drying step is to dry the mixed solution to give an absorbent composition. Any drying process may be used as long as the qualities of the absorbent composition may be maintained. For example, the drying step can be achieved by hot air drying, heat drying, vacuum drying, freeze drying, spray drying, or a combination thereof.

The absorbent composition is obtainable in the form of dry solid of various shapes, such as sheet and powder. When provided in a sheet form, the dry solid is preferably cut into 1 to 3 mm squares in view of improved handling as an absorbent material.

While the present invention has been described with particular reference to preferred embodiments thereof, it should be understood that the present invention is not construed as being limited to these embodiments, and various changes and modifications can be added thereto without departing from the spirit and scope of the invention.

The following clauses are further illustrative of the embodiments of the absorbent composition and the method of producing the same disclosed herein.

1. An absorbent composition containing cellulose nanofibers and a cellulose derivative, the cellulose derivative having a viscosity of 1000 mPa·s or higher in a 1 mass % aqueous solution at 25° C. and a degree of etherification of less than 0.9.

2. The absorbent composition according to clause 1, wherein the cellulose derivative is at least one member selected from the group consisting of carboxymethyl cellulose, carboxyethyl cellulose, methyl cellulose, hydroxypropyl cellulose, hydroxypropylmethyl cellulose, hydroxyethyl cellulose, and salts thereof.

3. The absorbent composition according to clause 1, wherein the cellulose derivative is at least one member selected from the group consisting of carboxymethyl cellulose, carboxyethyl cellulose, a carboxymethyl cellulose salt, and a carboxyethyl cellulose salt.

4. The absorbent composition according to clause 1, wherein the cellulose derivative is a carboxymethyl cellulose salt.

5. The absorbent composition according to clause 1, wherein the cellulose derivative is sodium carboxymethyl cellulose.

6. The absorbent composition according to any one of clauses 1 to 5, wherein the viscosity of the cellulose derivative is 4000 to 30000 mPa·s.

7. The absorbent composition according to any one of clauses 1 to 5, wherein the viscosity of the cellulose derivative is 6000 to 20000 mPa·s.

8. The absorbent composition according to any one of clauses 1 to 7, wherein the cellulose derivative has a degree of etherification of 0.4 to 0.8.

9. The absorbent composition according to any one of clauses 1 to 7, wherein the cellulose derivative has a degree of etherification of 0.5 to 0.75.
10. The absorbent composition according to any one of clauses 1 to 9, wherein the cellulose derivative has a mass average molecular weight of 5000 to 1,000,000, preferably 10,000 to 800,000, more preferably 100,000 to 600,000.
11. The absorbent composition according to any one of clauses 1 to 10, wherein the cellulose nanofibers have an average length of 500 to 5000 nm, preferably 1000 to 3000 nm.
12. The absorbent composition according to any one of clauses 1 to 11, wherein the cellulose nanofibers have an average diameter of 3 to 300 nm, preferably 5 to 100 nm.
13. The absorbent composition according to any one of clauses 1 to 12, wherein the cellulose nanofibers have a length to diameter ratio of 50 to 2500, preferably 75 to 2000, more preferably 100 to 1500.
14. The absorbent composition according to any one of clauses 1 to 13, having a cellulose nanofiber content C1 to cellulose derivative content C2 ratio, C1:C2, of 1:1 to 1:100.
15. The absorbent composition according to any one of clauses 1 to 13, having a cellulose nanofiber content C1 to cellulose derivative content C2 ratio, C1:C2, of 1:2 to 1:50.
16. The absorbent composition according to any one of clauses 1 to 13, having a cellulose nanofiber content C1 to cellulose derivative content C2 ratio, C1:C2, of 1:3 to 1:20.
17. The absorbent composition according to any one of clauses 1 to 16, being capable of absorbing at least 50 times, preferably 100 or more times, more preferably 200 or more times, its own weight in water.
18. A method for producing the absorbent composition according to any one of clauses 1 to 17, including the steps of mixing the cellulose nanofibers and the cellulose derivative in a liquid and drying the resulting mixed solution.
19. The method according to clause 18, wherein the mixed solution has a content of the cellulose nanofiber of 0.1 to 1 mass %, preferably 0.2 to 0.8 mass %.
20. The method according to clause 18 or 19, wherein the mixed solution has a content of the cellulose derivative of 0.1 to 1 mass %, preferably 0.2 to 0.8 mass %.

EXAMPLE

The present invention will now be illustrated in greater detail with reference to Examples. It should be understood that the present invention is not limited thereto. Unless otherwise noted, all the percentages are by mass.

Example 1

An aqueous dispersion of carboxy-modified CNFs (Rheocrysta from DKS Co., Ltd.; CNF concentration: 2.5%) and sodium carboxymethyl cellulose (CMC-Na) (Cellogen BSH-6 from DKS Co., Ltd.) were provided. The CNF aqueous dispersion, the CMC-Na, and ion exchanged water were mixed to prepare a CNFs/CMC-Na mixed solution having a CNF content of 0.4% and a cellulose derivative content of 0.4%. An about 50 mL portion of the mixed solution was uniformly applied to a 280 mm×200 mm×20 mm (t) metal plate, dried in an electric dryer at 105° C. for about 5 hours, and left to stand in a room temperature environment for about 30 minutes to form a dry film on the plate. The film was finely cut with scissors into squares of about 1.0 mm side, which were used as the absorbent composition of Example 1. The CNF content C1 to cellulose derivative content C2 ratio, C1:C2, of the absorbent composition, the viscosity of a 1% aqueous solution of the cellulose derivative (at 25° C.), and the degree of etherification of the cellulose derivative in Examples and Comparative Examples were determined by the above-described methods. The results are shown in Table 1 below.

Examples 2 and 3 and Comparative Examples 1 and 2

Absorbent compositions were prepared in the same manner as in Example 1, except for using CMC-Na having different viscosities in a 1% aqueous solution at 25° C. Specifically, the CMC-Na products used were:
Cellogen BSH-12 in Example 2,
Cellogen MP-60 in Example 3,
Cellogen 7A in Comparative Example 1, and
Cellogen HE1500 in Comparative Example 2, all available from DKS Co., Ltd.

Examples 4 to 6

Absorbent compositions were prepared in the same manner as in Example 2, except for changing the CNF content C1 to cellulose derivative content C2 ratio, C1:C2, as shown in Table 1.

Comparative Examples 3 and 4

Absorbent compositions were prepared in the same manner as in Example 1, except that the cellulose derivative was not used in Comparative Example 3 and that CNFs were not used in Comparative Example 4.
Evaluation of Gelation
A 0.03 g portion of each absorbent composition prepared was put in a 20 mL vial (screw type, from Maruemu Corp.), and 3.0 g of ion-exchanged water, which was 100 times the weight of the absorbent composition, was added thereto. The vial closed with a screw cap was shaken by hand for 5 seconds with its cap up to see whether gelation occurred. Shaking was continued while visually checking the progress of gelation for every 10 seconds. The contents of the vial were determined to have gelled when the contents did not drop in 30 seconds with the vial kept vertical with the cap down. The time from the addition of water to gelation (gelation time) was measured. A sample that did not gel in 60 minutes from the start of shaking was determined to be incapable of gelling. For those samples that were determined to be capable of gelling with 100 times the weight of water, the same test was repeated using 6.0 g of water (200 times the weight of the absorbent composition). Furthermore, a maximum liquid retention capacity of the absorbent composition was measured even for those samples that did not gel with 100 times or 200 times its own weight of water in 60 minutes from the start of shaking. Specifically, the vial was held upside down, and the amount of the liquid having dripped down from the vial was measured. The measured amount of the liquid was subtracted from the amount of ion exchanged water added to the vial before shaking to give the maximum liquid retention capacity of the absorbent composition. The gelation, gelling time, and maximum liquid retention capacity of each sample are shown in Table 1.

TABLE 1

|  |  | Example | | | | | | Comparative Example | | | |
| --- | --- | --- | --- | --- | --- | --- | --- | --- | --- | --- | --- |
|  |  | 1 | 2 | 3 | 4 | 5 | 6 | 1 | 2 | 3 | 4 |
| Absorbent Composition | Viscosity of Cellulose Derivative (mPa·s) | 1300 | 6500 | 8000 | 6500 | 6500 | 6500 | 6 | 1100 | — | 1300 |
|  | Degree of Etherification of Cellulose Derivative | 0.7 | 0.7 | 0.7 | 0.7 | 0.7 | 0.7 | 0.75 | 1.3 | — | 0.7 |
|  | C1:C2 | 1:1 | 1:1 | 1:1 | 1:2 | 1:10 | 2:1 | 1:1 | 1:1 | — | — |
| In 100 Times the Weight of Water | Gelation | yes | yes | yes | yes | yes | yes | no | no | no | no |
|  | Gelling Time (sec) | 70 | 170 | 60 | 90 | 50 | 190 | — | — | — | — |
| In 200 Times the Weight of Water | Gelation | no | no | yes | yes | yes | no | — | — | — | — |
|  | Gelling Time (sec) | — | — | 530 | 1020 | 120 | — | — | — | — | — |
| Max. Liquid Retention Capacity (mL) |  | 3.6 | 5.7 | 7.6 | 7.7 | 12.5 | 6.2 | 1.1 | 1.8 | 1.1 | 0 |
| Ratio of Max. Liquid Retention Capacity to Weight of Absorbent Composition (times) |  | 120 | 190 | 253 | 257 | 417 | 207 | 37 | 60 | 37 | — |

As is apparent from the results in Table 1, the absorbent compositions of Examples 1 through 6 were capable of gelling 100 times their own weight of ion exchanged water. That is, the absorbent compositions of Examples 1 to 6 were capable of absorbing and retaining 100 times their weight of water. Such high performance is believed to be due to the high dispersibility of CNFs in the absorbent compositions. Thus, the absorbent compositions of Examples 1 to 6 are proved by the results in Table 1 to have sufficient absorption performance as an absorbent material for use in absorbent articles, such as diapers.

The results of Examples 1 to 3 demonstrate that increasing the viscosity of the cellulose derivative in a 1% aqueous solution at 25° C. is effective in improving the absorption performance of the absorbent composition.

The results of Examples 2 and 4 to 6 show that the absorbent compositions of which the cellulose derivative content C2 is higher than the CNF content C1 are more effective in improving the liquid retaining performance that those not so formulated.

Furthermore, cellulose derivatives having too low a viscosity in a 1% aqueous solution at 25° C. or too high a degree of etherification fail to produce the water absorbing and retaining effects.

INDUSTRIAL APPLICABILITY

The absorbent composition of the present invention exhibits excellent absorption performance. The method of the present invention produces an absorbent composition having excellent absorption performance.

The invention claimed is:

1. An absorbent composition, comprising:
   cellulose nanofibers; and
   a cellulose derivative comprising a carboxy cellulose or a carboxy cellulose salt;
   wherein:
   the cellulose derivative has a viscosity of 6500 to 8000 mPa·s in a 1 mass % aqueous solution at 25° C.; and
   the cellulose derivative has a degree of etherification of 0.7 or less; and
   the absorbent composition has a ratio C1:C2 of 1:1 to 1:10, wherein:
   C1 is a content by mass of the cellulose nanofibers in the absorbent composition; and
   C2 is a content by mass of the cellulose derivative in the absorbent composition.

2. The absorbent composition according to claim 1, wherein the cellulose derivative is selected from the group consisting of carboxymethyl cellulose, carboxyethyl cellulose, a carboxymethyl cellulose salt, and a carboxyethyl cellulose salt.

3. The absorbent composition according to claim 1, wherein the cellulose derivative comprises a carboxymethyl cellulose salt.

4. The absorbent composition according to claim 1, wherein the cellulose derivative comprises sodium carboxymethyl cellulose.

5. The absorbent composition according to claim 1, wherein the degree of etherification of the cellulose derivative is 0.4 to 0.7.

6. The absorbent composition according to claim 1, wherein the degree of etherification of the cellulose derivative is 0.5 to 0.7.

7. The absorbent composition according to claim 1, wherein the cellulose derivative has a mass average molecular weight of 5,000 to 1,000,000.

8. The absorbent composition according to claim 1, wherein the cellulose nanofibers have an average length of 500 to 5,000 nm.

9. The absorbent composition according to claim 1, wherein the cellulose nanofibers have an average diameter of 3 to 300 nm.

10. The absorbent composition according to claim 1, wherein the cellulose nanofibers have a length to diameter ratio of 50 to 2500.

11. The absorbent composition according to claim 1, wherein the ratio C1:C2 is 1:2 to 1:10.

12. The absorbent composition according to claim 1, wherein the ratio C1:C2 is 1:3 to 1:10.

13. The absorbent composition according to claim 1, wherein the absorbent composition is capable of absorbing at least 50 times its own weight in water.

14. A method for producing the absorbent composition according to claim 1, comprising:
    mixing the cellulose nanofibers and the cellulose derivative in a liquid to obtain a mixed solution; and
    drying the mixed solution.

15. The method according to claim 14, wherein a content of the cellulose nanofibers in the mixed solution is 0.1 to 1 mass %.

16. The method according to claim 14, wherein a content of the cellulose derivative in the mixed solution is 0.1 to 1 mass %.

\* \* \* \* \*